United States Patent [19]

Prahl

[11] Patent Number: 4,572,196
[45] Date of Patent: Feb. 25, 1986

[54] ARCH SUPPORT ESPECIALLY FOR THE THERAPY OF PES VALGUS IN CHILDREN

[75] Inventor: Jan Prahl, Rullfstor, Fed. Rep. of Germany

[73] Assignee: IPOS Gesellschaft für integrierte Prothese-Entwicklung und orthopädietechnischen Service mbH & Co. KG, Lüneburg, Fed. Rep. of Germany

[21] Appl. No.: 569,798

[22] Filed: Jan. 11, 1984

[30] Foreign Application Priority Data

Jan. 10, 1984 [DE] Fed. Rep. of Germany ... 8400457[U]

[51] Int. Cl.⁴ .............................................. A61F 5/14
[52] U.S. Cl. .................................... 128/581; 128/583; 128/586; 128/591
[58] Field of Search ............ 128/581, 586, 583, 80 D, 128/80 H, 80 J, 80 E, 80 F, 166, 166.5, 165, 584, 585, 594, 595, 614, 615; D24/42, 64; 2/241, 239

[56] References Cited

U.S. PATENT DOCUMENTS

| | | | |
|---|---|---|---|
| 1,013,992 | 1/1912 | Foster | 128/614 |
| 1,596,146 | 8/1926 | Block | 128/80 D |
| 3,013,564 | 12/1961 | Levey | 2/241 |
| 3,863,272 | 2/1975 | Guille | 2/239 |
| 4,333,472 | 6/1982 | Tager | 128/581 |

Primary Examiner—Richard J. Apley
Assistant Examiner—James Prizant
Attorney, Agent, or Firm—Toren, McGeady, Stanger, Goldberg & Kiel

[57] ABSTRACT

The invention relates to an incompressible, formed elastic body which adjusts itself to the dynamic movement of the foot and is secured as an integral part of a stocking sole.

3 Claims, 6 Drawing Figures

ARCH SUPPORT ESPECIALLY FOR THE THERAPY OF PES VALGUS IN CHILDREN

BACKGROUND OF THE INVENTION

The invention relates to an arch support especially for the therapy of pes valgus in children.

Arch supports for the purpose of correcting static foot complaints are made of a great variety of materials. Now metal insoles or arch supports, consisting of combinations of wood, leather, and cork dominate in the medical care of pes valgus in children. However, such conventional correcting supports have certain disadvantages when used by children. Furthermore, soft arch supports, especially made of foam material, are known for use by adults.

Supply of arch supports for children is of considerable importance regarding corrective effects, viz. the correction of pes valgus. So far, mainly arch supports made of cork/leather with metal inlays have been used. Such supports, however, have proved to be disadvantageous in that they compress the muscular system of the foot in consequence of their hard supporting effects, thus leading to a relative inactivity atrophy. Beyond that callosity, pressure points, and other strains on the child's foot usually develop at the edges of such supports. The most serious disadvantage is, however, the mentioned muscular atrophy.

It should be noted that children, using such arch supports for the correction of pes valgus, often lose their arch supports. The supports are often removed from shoes on the way to school or they are not changed when other shoes, for example, rubber boots, slippers, walking shoes or sandals are worn. Very often children run around at home in stockings only, in which cases the arch supports are ineffective. In these circumstances the corrective use of the arch supports is rather limited.

Another disadvantage of the so-called hard arch supports for children lies in the fact that the metal parts cut into the shoe material, particularly at the insoles, thus resulting quickly in damage to the shoes. Also the dynamic moving process of the child is adversely affected by such hard corrective means.

BRIEF SUMMARY OF THE INVENTION

The invention solves the problem by providing a nonfatiguing arch-support rendering the effectiveness of a metallic arch support without restricting the movement of the child's foot by a fixed arrangement and by which the natural rolling movement of the foot and its adjustment to different terrain are essentially not affected and the time of corrective use exceeds by far that of known arch supports, and this orthopedic aid will easily enable correction.

According to the invention this problem is solved by providing an arch support, especially for therapy of pes valgus in children, consisting of a homogenous, incompressible and elastic silicone caoutchouc or rubber whidh adjusts itself to the dynamic movement of the foot and which is joined to the part of a stocking, forming the sole, by glueing or vulcanization. Proceeding on the assumption that the heel-bone itself is placed on a laterally extending slightly inclined plane, the anklebone and the heel-bone will be shifted by such a formed arch support from the pathological pes valgus position to a normal varus position. The arch support is nonfatiguing and renders the supporting effects of a metallic arch support without restricting the movement of the child's foot by a fixed arrangement. Natural rolling movements of the foot and adjustments of the foot to different terrain are essentially not affected because of the flexibility of the arch support, and, as a result, inactivity atrophy, mentioned at the beginning, will be largely reduced by this dynamic arch support.

The arch support itself will not be put in the shoe but will be jointed permanently to the child's stocking by glueing or vulcanization. Such an orthopedic stocking will be put on by the child in the morning and the child will wear the stocking during the whole day. Slippers, walking shoes, rubber boots, sandals and running without shoes will not adversely affect the corrective functions of such combination of arch support and stockings. The time of use of such a corrective arch support will be increased considerably.

The combination stocking/arch support creates a functional unit which, put on in the morning, will remain on the foot for the whole day. Adding correction adjustments is possible. All dynamic foot movements are set free by the precise combination of the elastic arch support. This orthopedic stocking may be washed like ordinary stockings.

Further advantageous embodiments of the invention can be gathered from the subclaims.

BRIEF DESCRIPTION OF THE DRAWINGS

The subject matter of the invention is illustrated by way of example in the attached drawings, wherein.

DETAILED DESCRIPTION OF THE INVENTION

Figure 1:
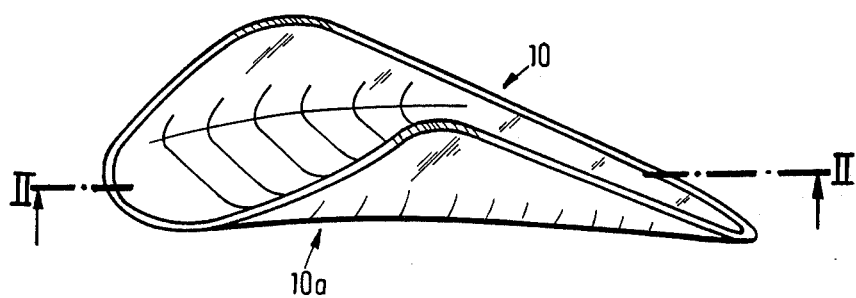
FIG. 1 is a perspective view of the arch support.
Figure 2:
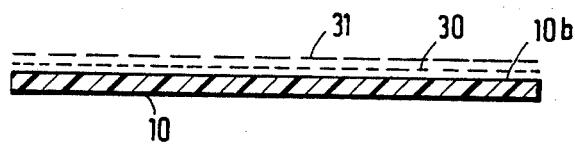
FIG. 2 is a vertical sectional view along line II—II of FIG. 1.

The arch support 10, shown in FIG. 1, consists of a formed body 10a, especially adapted to the feet of children, and made of incompressible, elastic material, in particular of silicone caoutchouc or rubber, so that the arch support adjusts itself to the dynamic movement of the foot. In order to enable the attachment of the arch support 10 to a child's foot, the side 10b of the formed body 10a, facing toward the foot, is provided with a self-adhesive coating 30, covered by a strippable protective foil 31 (FIG. 2). In this way it is possible to attach the arch support not only directly to the sole of the foot but also to stockings, hoses, socks etc., thus avoiding loss of the arch support. Particularly in the case of changing shoes it will be assured that use of the arch support will continue.

Figure 3:
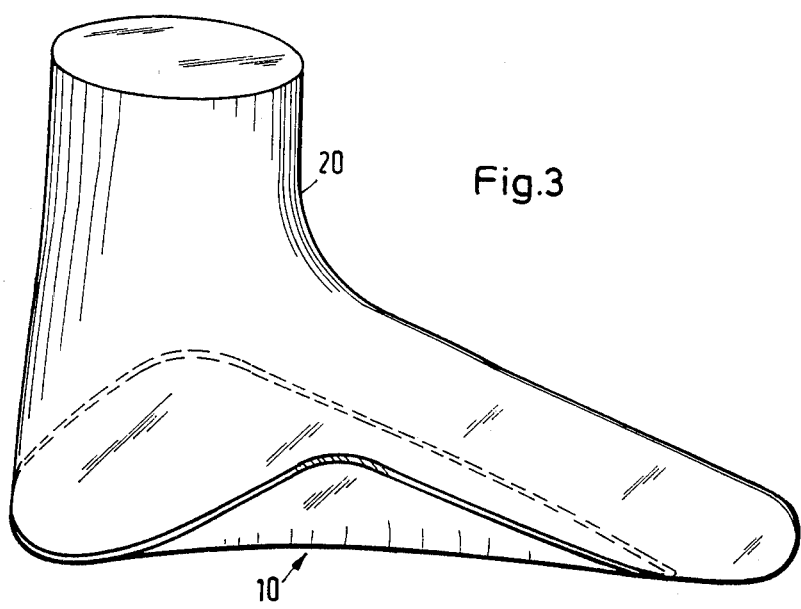
FIG. 3 is a perspective view of the arch support integrated with a stocking.

According to the embodiment shown in FIG. 3, the formed body 10a is an integral component of the sole of a knitted stocking 20 with the formed body 10a firmly jointed to the stocking by glueing or vulcanization.

Figure 4:
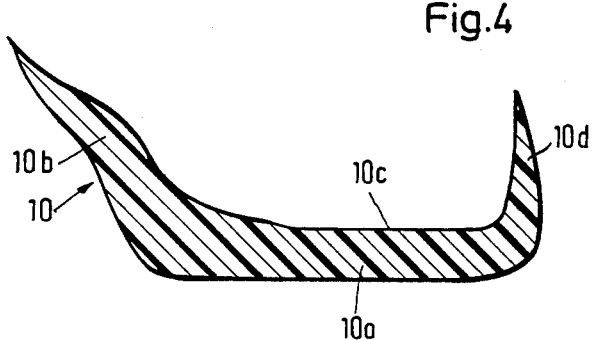
FIG. 4 is a vertical cross-sectional view of an arch support of normal design.
Figure 5:
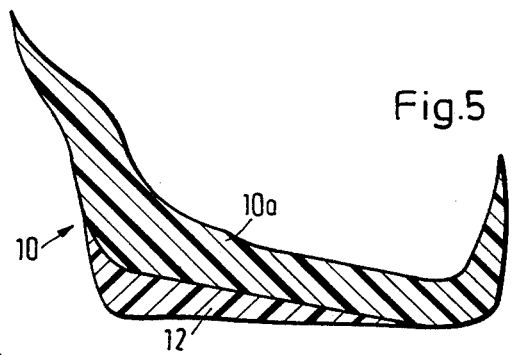
FIG. 5 is a vertical cross-sectional view of an arch support with one correction piece.
Figure 6:
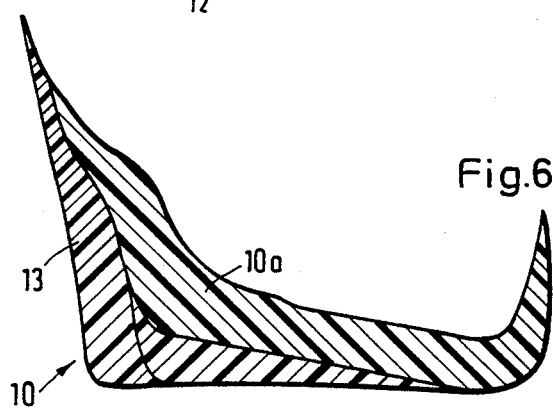
FIG. 6 is a vertical cross-sectional view of an arch support with an additional correction piece.

As shown in FIGS. 5 and 6 the formed body 10a of the arch support 10 can be provided with correction pieces. The embodiment shown in FIG. 4 illustrates that the heel-bone is raised by a supporting section 10b' at the sustentaculum tali. In this case the heel support 10c extends horizontally. A laterally extending elastic raised support edge 10d fills the space between foot and shoe.

According to the embodiment shown in FIG. 5 the arch support has been taken over from FIG. 4. The heel-bone support 10c is additionally provided with a correction piece 12 formed as a supination wedge. The correction piece 12 is provided with a self adhesive coating on the fixing side which is covered by a strippable protective foil which is removed if the correction piece 12 is added to the formed body 10a of the arch support 10. Also other fixing methods, such as glueing and vulcanization can be used.

In FIG. 6 the formed body 10a of FIG. 5 is provided with a further correction piece 13 by which a supporting effect on the naviculare bone is achieved. Fixing of the correction piece 13 is performed in the same manner as for correction piece 12.

What is claimed is:

1. An orthopaedic arch support, in particular for therapy of pes valgus in children, comprising, in combination, a stocking and a formed body shaped as a foot support, said stocking having a sole part, said formed body is made of a homogenous incompressible elastic silicone caoutchouc adjustable to the dynamic movements of the foot, said formed body is adhered to the surface of the sole part of said stocking, said formed body includes a horizontally extending heel support having a first side and a second side with each of said first and second sides extending in the long direction of the foot, a sustentaculum tali-supporting section extending upwardly from the first side of said heel support, an upwardly extending elastic support edge located along the second side of said heel support spaced laterally from said sustentaculum tali-supporting section, a first correction piece in the form of a supination wedge located below in contact with and secured to said heel support, a second correction piece for supporting the navicular bone extending upwardly from said first correction piece and in contact with the outer surface of said sustentaculum tali-supporting section, and said first and second connection pieces being detachable and replaceable.

2. Arch support, as set forth in claim 1, wherein said formed body is secured to said stocking by glueing.

3. Arch support, as set forth in claim 1, wherein said formed body is secured to said stocking by vulcanization.

* * * * *